(12) United States Patent
Leino et al.

(10) Patent No.: US 10,172,792 B2
(45) Date of Patent: Jan. 8, 2019

(54) HYDROGEL COMPOSITE DEPOT FORMULATION

(71) Applicant: DelSiTech Oy, Turku (FI)

(72) Inventors: Lasse Leino, Merimasku (FI); Harry Jalonen, Turku (FI); Ari-Pekka Forsback, Turku (FI); Mika Jokinen, Turku (FI); Panu Noppari, Espoo (FI)

(73) Assignee: DelSiTech Oy, Turku (FI)

( * ) Notice: Subject to any disclaimer, the term of this patent is extended or adjusted under 35 U.S.C. 154(b) by 0 days.

(21) Appl. No.: 15/770,034

(22) PCT Filed: Oct. 21, 2016

(86) PCT No.: PCT/FI2016/050745
§ 371 (c)(1),
(2) Date: Apr. 20, 2018

(87) PCT Pub. No.: WO2017/068245
PCT Pub. Date: Apr. 27, 2017

(65) Prior Publication Data
US 2018/0311150 A1    Nov. 1, 2018

(30) Foreign Application Priority Data
Oct. 22, 2015  (FI) ..................................... 20155750

(51) Int. Cl.
| | | |
|---|---|---|
| *A61K 9/00* | (2006.01) | |
| *A61K 9/10* | (2006.01) | |
| *A61K 9/16* | (2006.01) | |
| *A61M 5/32* | (2006.01) | |
| *A61K 31/522* | (2006.01) | |

(52) U.S. Cl.
CPC .......... *A61K 9/0024* (2013.01); *A61K 9/0048* (2013.01); *A61K 9/10* (2013.01); *A61K 9/1611* (2013.01); *A61K 31/522* (2013.01); *A61M 5/329* (2013.01)

(58) Field of Classification Search
CPC .... A61K 31/522; A61K 47/02; A61K 9/0024; A61K 9/1611
See application file for complete search history.

(56) References Cited

U.S. PATENT DOCUMENTS

2012/0104639 A1*   5/2012  Traynor ................. A01N 25/28
                                                              264/4.32
2014/0363509 A1*  12/2014  Mortera ................. A61K 31/00
                                                              424/489

FOREIGN PATENT DOCUMENTS

| KR | 20120138908 | 12/2012 |
|---|---|---|
| WO | 9745367 | 12/1997 |
| WO | 2014207304 | 12/2014 |
| WO | 2015020240 | 2/2015 |

OTHER PUBLICATIONS

Lim et al., "An Injectable Liquid Crystal System for Sustained Delivery of Entecavir," 490 Int. J. Pharm. 265 (2015).

* cited by examiner

*Primary Examiner* — Mark V Stevens
(74) *Attorney, Agent, or Firm* — James C. Lydon

(57) ABSTRACT

This invention relates to a depot formulation comprising a biodegradable silica hydrogel composite incorporating a nucleotide or nucleoside analog reverse transcriptase inhibitor, wherein the silica hydrogel composite is obtainable by mixing silica particles comprising said nucleotide or nucleoside analog reverse transcriptase inhibitor and having a maximum diameter of ≤1 000 μm, as such or as a suspension, with silica sol wherein the hydrogel composite is non-flowing and structurally stable when stored at rest and shear-thinning when shear stress is applied by injection. The present invention also relates to use of the depot formulation for treatment of chronic viral infections and prevention of chronic viral reinfection. The present invention further relates to a prefilled syringes comprising said depot formulation.

24 Claims, 4 Drawing Sheets

HYDROGEL COMPOSITE DEPOT FORMULATION

FIELD OF THE INVENTION

This invention relates to a depot formulation comprising a biodegradable silica hydrogel composite incorporating a nucleotide or nucleoside analogue reverse transcriptase inhibitor and the depot formulation is feasible for drug delivery. The invention also relates to a prefilled syringe comprising the depot formulation.

BACKGROUND OF THE INVENTION

The publications and other materials used herein to illuminate the background of the invention, and in particular, cases to provide additional details respecting the practice, are incorporated by reference.

Several virus infections are major global public health problems. Some viruses cause chronic infections and carriers of untreated chronic infections are at increased risk of developing long-term complications, such as hepatic failure or cancer. It has been estimated that every year more than 1 million chronic Hepatitis B virus (HBV) infection patients die from the liver complications caused by the infection. Interferons and antiviral nucleoside and nucleotide analogues are used to cure or to suppress the replication activities of virus to keep the infection inactive and to prevent the progression of complications. The most common treatment options include daily oral self-administration or daily injections (or several weekly injections). Due to the long-term or even life-long drug therapy, daily self-administration requires strong commitment from the patient. This is also a challenge from the viewpoint of patient compliance as any longer treatment break promote antiviral drug resistance and recurrence is likely to occur when the suppressive effect of antivirals is omitted. Hence, there is an unmet need for long-term depot formulations in the treatment of virus infections and especially for minimally invasive ones, such as injectable formulations with relatively long administration intervals.

Silica gels have widely been used as a carrier material for controlled drug delivery and they can be processed into different dosage forms and the dosage forms can be combined to result in silica-silica composites with specific properties. Sol-gel derived silica microparticles with encapsulated drugs can be combined with a silica sol to form an injectable hydrogel depot composite for controlled delivery of antiviral drugs.

WO 2014/207304 by Jokinen et al, discloses shear-thinning combined hydrogel compositions formed from spray-dried silica microparticles with encapsulated agents and silica sols.

KR20120138908 discloses entecavir-containing microspheres and process for preparing the same.

WO2015020240 discloses entecavir microspheres and pharmaceutical composition for parenteral administration containing same.

Recently, a pegylated alpha-interferon was developed and, launched by Genentech/Roche for once-a-week injection treatment of chronic HBV infection. However, interferon therapy is associated with frequent systemic side effects, and it cannot be administered to patients with decompensated liver function.

OBJECT AND SUMMARY OF THE INVENTION

One object of the present invention is to provide a depot formulation comprising a biodegradable silica hydrogel composite incorporating a nucleotide or nucleoside analogue reverse transcriptase inhibitor.

Another object of the present invention is to provide the depot formulation for use in treatment.

The present invention provides a depot formulation comprising a biodegradable silica hydrogel composite incorporating a nucleotide or nucleoside analogue reverse transcriptase inhibitor, wherein the silica hydrogel composite is obtainable by mixing a) silica particles comprising said nucleotide or nucleoside analogue reverse transcriptase inhibitor and having a maximum diameter of ≤1 000 μm, as such or as a suspension, with b) a silica sol wherein i) said silica sol has a solid content of ≤5 wt-%, ii) said silica hydrogel composite comprises up to 85 wt-% of said silica particles, and iii) said hydrogel composite is non-flowing and structurally stable wen stored at rest and shear-thinning when shear stress is applied by injection.

The present invention also provides the depot formulation for use in the treatment of chronic viral infections and prevention of chronic viral reinfection.

The present invention further provides a prefilled syringe comprising said depot formulation.

BRIEF DESCRIPTION OF THE DRAWINGS

FIG. 1 illustrates cumulative release of entecavir and dissolution of silica from hydrogel composite.

FIG. 2 illustrated average complex modulus (G*) for hydrogel composites as a function of storage time.

FIG. 3 illustrates shear-thinning property by dynamic viscosity at different shear rates for a hydrogel composite.

FIG. 4 illustrates the structure of the hydrogel composite prior to injection by loss factor (tan δ=G"/G').

FIG. 5 illustrated the structure of the hydrogel composite after the injection by loss factor (tan δ=G"/G').

FIG. 6 illustrates plasma entecavir concentrations in beagle male dogs administered entecavir in a hydrogel composite.

FIG. 7 illustrates plasma entecavir concentrations in beagle female dogs administered entecavir in a hydrogel composite.

DETAILED DESCRIPTION OF THE INVENTION

The inventors have surprisingly demonstrated that a nucleotide or nucleoside analogue reverse transcriptase inhibitor incorporated into silica microparticles and embedded in a silica gel to result in a silica hydrogel composite performing outstandingly as an injectable depot formulation for delivering a nucleotide or nucleoside analogue reverse transcriptase inhibitor to patients in need thereof.

Microparticles can be prepared by many different methods. Microparticles (often spherical particles, microspheres) are typically small particles with diameters in the micrometer range (typically 1 μm to 1000 μm). There are several direct techniques that are commonly used to prepare or manufacture microparticles with a controlled particle size distribution, such as spray-drying (often followed by centrifugal separation of the microparticles in cyclones), single emulsion, double emulsion, polymerization, coacervation phase separation and solvent extraction methods. By using these techniques, a small volume fraction of submicron particles (commonly between 0.5-1.0 μm) may be included in the resulting product, but their proportion is usually very low, often less than 1 volume-%. Thus, their effect, e.g. in controlled release microparticle formulations, is minor. It is also possible to prepare microparticles by casting or by, crushing larger structures to microparticles, but in that case the size and form of the resulting particles may vary a lot and additional preparation steps, such as tumbling and particle sizing are needed.

Silica microparticles of the silica-silica composites have a role in the controlled release of drugs and the hydrogel structure ensures both stability and injectability of the resulting composite. Although stable at rest, e.g., as stored in a prefilled syringe, the hydrogel composite structure is so loose that it is shear-thinning when the hydrogel composite is injected from ready-to-use syringes through thin needles. This combination of properties provides a minimally invasive, long-term treatment of viral infections.

Terms

Gel should be understood in the context of this application to be a homogeneous mixture of at least one solid phase and one liquid phase, i.e., a colloidal dispersion, where solid phase(s), e.g. silica as such and/or as partly or fully hydrolysed, is the continuous phase and the liquid(s), e.g. water, ethanol and residuals of silica precursors, is homogeneously dispersed in the structure. The gel is viscoelastic and the elastic properties dominate, which is indicated by rheological measurements under small angle oscillatory shear. The elastic properties dominate and the structure is non-flowing when the loss factor (or the loss tangent), tan $\delta=(G''/G')$, is less than 1. The combined effect of the elastic modulus G' and the viscous modulus G" can also be expressed in the form of complex modulus (or complex shear modulus), $G^*=G'+iG''$.

The hydrogel should be understood to be a gel, where the liquid phase is water or water-based containing more than 50 weight-% (wt-%) of water. Typically the liquid phase of the hydrogel comprises >65% wt-%, more typically >90 wt-% and most typically >95 wt-% of water. The liquid phase can additionally comprise other liquids, typically organic solvents, e.g. ethanol. Typically the concentration of such solvents, e.g. ethanol, is <10 wt-%, more typically <3 wt-% and most typically <1 wt-%. In the context of this invention the composite of the invention is considered a hydrogel since it fulfils the basic criteria of a hydrogel. Accordingly, when referring to the hydrogel composite of the invention this referral is equivalent to a referral to the composite of the invention. In the context of this invention the silica hydrogel composite of the invention preferably comprises 20 to 80 wt-%, more preferably 30 to 70 wt-%, and most preferably 40 to 60 wt-% of water.

The sol should be understood to be a homogeneous mixture of at least one liquid phase and one solid phase, i.e., a colloidal dispersion, where the liquid phase(s), e.g. water, ethanol and residuals of silica precursors, is the continuous phase and the solid phase(s), e.g. colloidal particles of silica and/or as partly or fully hydrolysed silica and/or aggregates of said particles are homogeneously dispersed in the said liquid phase characterized in that the sol has clear flow properties and the liquid phase is dominating. A suspension can also be called a sol especially if the solid particles are colloidal, being smaller than 1 μm in diameter. In the context of the present invention, however, the term sol refers to a colloidal dispersion wherein the solid particles are <50 nm and the term suspension refers to a dispersion wherein the solid particles are >50 nm.

Injectable Gel or Hydrogel in a context of this application is a rheological property of a composition. Before injection, e.g., as stored in a syringe and/or in an aluminium foil at temperatures <37° C., e.g., at room temperature (at 20-25° C.), or at refrigerator temperatures (at 3-6° C.) the composition is a gel, i.e., the elastic modulus (measured under small angle oscillatory shear) G' is greater than the viscous modulus G" and the loss factor, tan $\delta=(G''/G')$, is less than 1. Although the hydrogel composite structure is a gel-like structure and the composite structure remains stable and non-flowing as stored at rest, the gel structure is so loose that it is shear-thinning when shear stress, e.g., in the form of injection through a needle from a syringe is applied, e.g., by using 25G needle (0.50 mm×25 mm).

Injectable means, in the context of this invention, administrable via a surgical administration apparatus, e.g. a needle, a catheter or a combination of these.

Shear-thinning in the context of this application is a rheological property of a composition. Whenever the shear stress or shear rate of such a composition is altered, the composition will gradually move towards its new, equilibrium state and at lower share rates the shear thinning composition is more viscous, and at higher shear rates it is less viscous. Thus shear-thinning refers to an effect where a fluid's viscosity, i.e. the measure of a fluid's resistance to flow, decreases with an increasing rate of shear stress.

Depot formulation referred to in the application is defined to be the administration of a sustained-action drug (active agent) formulation that allows slow release and gradual absorption, so that the active agent can act and is released in the body for longer periods of times, i.e., from several days to several months. Depot, formulations are administered parenterally, either by subcutaneous, intramuscular, peritoneal or ocular implantation or injection.

The term silica refers to amorphous $SiO_2$ that is preferably prepared by a sol-gel process. The sol-gel derived silica refers to silica prepared by the sol-gel process wherein the silica is prepared from liquid phase precursors, such as alkoxides, alkylalkoxides, aminoalkoxides or inorganic silicate solutions, which by hydrolysis and condensation reactions form a sol that turns to a gel or forms a stable sol. The liquids in the stable silica sol can be evaporated, which results in the formation of a powder consisting typically of colloidal silica particles. The resulting gels/particles can be optionally aged, dried and heat-treated and if heat-treated, preferably below 700° C. The sol-gel derived silica prepared below 700° C. is commonly amorphous. The heat treatment is typically skipped if the gel contains a biologically active agent, such as drugs and active pharmaceutical ingredients. The formed gel is then typically only aged (typically at ≤40° C.) and dried (typically at ≤40° C.) The sols can be let to gel in a mould for form-giving. The sol-gel derived silica can also be prepared by processing to different morphologies by simultaneous gelling, aging, drying and form-giving, e.g. by spray-drying to microparticles, by dip/drain/spin-coating to films, by extrusion to monolithic structures or by spinning to fibres.

The term silica sol refers to a suspension, i.e., mixture of a liquid (the continuous phase) and a solid phase (the dispersed phase), where the solid phase is comprised of silica particles and/or aggregated silica particles, where the particle size of the silica particles and/or aggregates is typically below 1 μm, i.e., the silica particles and/or particle aggregates are colloidal. A silica sol is commonly prepared from alkoxides or inorganic silicates that, via hydrolysis, form either partly hydrolysed silica species or fully hydrolysed silicic acid. The liquid phase is typically comprised of water and hydrolysis and condensation products, such as ethanol. Subsequent condensation reactions of SiOH-containing species lead to formation of larger silica species having an increasing amount of siloxane bonds. These species form nanosized, colloidal particles and/or particle aggregates. Depending on the conditions the silica sol remains as a stable colloidal suspension or it turns into a gel.

The term biodegradation refers to erosion, i.e., to gradual degradation of the matrix material, e.g., silica in the body. The degradation occurs preferably by dissolution in the body fluids.

Encapsulated agents should be understood to be drugs, active pharmaceutical ingredients (API) and other functional, therapeutic and biologically active agents that are inside of the sol-gel derived silica materials.

Nucleotide or nucleoside analogue Reverse Transcriptase Inhibitor refers to a class of antiretroviral drugs used to treat HIV infection or AIDS, and hepatitis B. RTIs inhibit activity of reverse transcriptase, a viral DNA polymerase that is required for replication of HIV and other retroviruses. Nucleoside analogues that are phosphorylated at the 5' site are often referred to as nucleotide analogues.

Gel point shall be, understood to mean the time point when the sol that is flowing turns to a gel that is viscoelastic and the elastic properties dominate, which is indicated by rheological measurements under small angle oscillatory shear that the elastic modulus, G' is greater than the viscous modulus and the loss factor is less than 1. The viscoelastic properties are commonly measured with a rheometer (a measuring device for determination of the correlation between deformation, shear stress and time) by the oscillatory shear, where shear stresses are small (small angles of deformation). The total resistance in small oscillatory shear is described by the complex modulus (G*). The complex modulus (or complex shear modulus), contains two components (G*=G' iG"): 1) elastic modulus, also called storage modulus, G' that describes that material has some elastic properties that are characteristic for a solid material, i.e., the gel system will gain energy from the oscillatory motion as long as the motion does not disrupt the gel structure. This energy is stored in the sample and is described by elastic modulus; 2) viscous modulus, also called loss modulus, G" that describes flow properties, i.e., a system, e.g. a silica sol that will in an oscillatory shear create motion between the ingredients of the sol describing the part of the energy, which is lost as viscous dissipation. As G*=G' a material is called elastic and as G*=G" a material is called viscous. At the gel point, the elastic modulus, G' becomes larger than the viscous modulus, G". As G'>G", a viscoelastic material is called semisolid and correspondingly as G">G, a viscoelastic material is called semi-liquid. The magnitude of the elastic and viscous modulus depends on the shear stress, which depends on the applied strain (small angle deformation) and frequency (of the oscillatory shear). The measurements are conducted by ensuring an adequate signal for a specific measuring system, i.e., a strain sweep is commonly done at constant frequencies to find the proper signal and the linear viscoelastic region for the rheometer system and then the actual measurements are done at constant strain with varying frequency. The varying frequencies give varying elastic and viscous modulus and the measurement show whether the solid or liquid phase dominates. It is also typical that the elastic modulus increases fast after the gel point if the surrounding conditions are not significantly changed, e.g. 100-700 fold increase in G' within few minutes after the gel point is typical for gels formed from acidic sols near room temperature, e.g. for a R15 sol at pH=2 that turns to a gel (R=water-to-alkoxide molar ratio). For larger R-values, such as R150 and R400, the elastic modulus, G' remains on a low level even after the gel point and increase of G' is not fast, which makes it possible to have gel structures that remain injectable with thin needles. In the form of a gel after the defined gel point, the solid state dominates, but the system still contains varying amounts of liquids and the material is typically soft and viscoelastic before drying, and hard and brittle if it is extensively dried. In the form of a sol, the liquid state dominates, but the system contains varying amounts of solid phase(s) and the system is still flowing. Before the gel point it is typical that a steep increase in dynamic viscosity and elastic modulus is observed, which continues to rise after the gel point as the structure is developing. In the context of the present invention gel point of the composite of the invention has been reached prior to obtaining the injectable gel of the invention.

Non-flowing and structurally stable when stored at rest refers to the stable composite hydrogel structure which is comprised of silica particles in the silica hydrogel. The stability is indicated by rheological measurements under small angle oscillatory shear by the elastic modulus, G' that is greater than the viscous modulus and the loss factor that is less than 1. When the elastic modulus is greater than the viscous modulus and the loss factor is less than 1, the structure is non-flowing. The non-flowing structure ensures the stability of the composite hydrogel structure by preventing the phase separation of the silica particles. In other words, the silica particles are embedded in the silica hydrogel and they do not, e.g., precipitate or separate on the bottom of a vessel, e.g., a syringe, where the hydrogel composite is stored, typically at temperatures ≤25° C. Although the composite hydrogel structure is non-flowing as stored at rest, e.g., in a prefilled, ready-to-use syringe, the structure is so loose that it is shear-thinning, and hence injectable through thin needles, as shear stress is applied on the hydrogel composite by injection.

FEATURES OF THE INVENTION

The present invention, an injectable silica-silica composite depot comprising silica microparticles (with encapsulated active pharmaceutical ingredient) embedded in a silica hydrogel, addresses typical practical challenges of microparticle-based drug delivery. Other challenges, which are of particular importance in the long-term treatment of virus infections, i.e. the patient compliance and the importance of unbroken antiviral drug treatment, are also met by the present invention by providing an easy-to-use and ready-to-use composite that is minimally invasive due to possibility to inject the composite through a thin needle from a syringe less frequently than any other medical product used in antiviral therapy.

Microparticles (typical size from 1 μm to 1000 μm) are so large that, e.g. a typical microparticle suspension with a water-based solution as a continuous phase will be destabilized relatively fast. Colloidal particles (size 1-1000 nm) are affected by the Brownian motion and it is relatively easy to form stable suspensions, but the effect is negligible on the microparticles. The phase separation occurs typically by the sedimentation of microparticles or if the microparticle density is clearly lower than that of the liquid, they may also be floated onto surface. The rate of separation depends on many factors; microparticle size, density of the microparticles and the continuous phase (liquid), microparticle concentration in the liquid and dynamic viscosity of the continuous phase. Near the particle size of 1 μm typical polymeric or ceramic microparticles in water-based suspensions separate within some days to weeks and when the particle size is larger than 10 μm, the separation occurs within some minutes to some days depending on the density differences between the microparticles and on the viscosity of the continuous phase (liquid). Thus, it is difficult to form long-lasting stable microparticle suspensions with common water based solutions, like saline or buffers. The common method is to increase the viscosity of the continuous phase (liquid) to retard the separation. However, in spite of the increased viscosity, there is always a risk for separation in a long-term storage when the continuous phase is a liquid, which is always more or less flowing. This is an important task to take into account if a long shelf-life is expected and it is usually required for drug formulations.

One can also design a system where the microparticles and the liquid are combined shortly before the administration, but this is not a desired option because of risks associated with mixing the components before administration. Good mixing of the microparticles in the liquid is of crucial importance both with respect to the safety and injectability. If the suspension is not well mixed and stable enough, both the correct dose and injectability of the suspension are at risk.

Because the present invention is specifically designed for minimally invasive administration, the hydrogel composite depot is designed to be a ready-to-use formulation. To use a hydrogel as a continuous phase (silica microparticles are embedded in the hydrogel) instead of a liquid ensures long-term composite stability, injectability and the correct dose. However, this brings along another challenge. The hydrogel composite has to retain its non flowing gel structure at rest (at storage conditions) to ensure the stability, but it has to be at the same time injectable, e.g., one has to be able to inject the hydrogel composite through thin needles from a syringe. It means that the hydrogel composite has to be shear-thinning (dynamic viscosity, with SI-unit Pas, decreases with increasing shear rate in the rotational measuring modes in rheometers) when shear stress is applied, e.g., by injecting. Thus, the present invention introduces a silica-silica hydrogel composite that is non-flowing at rest, but shear-thinning and flowing, when shear stress is applied. This is possible due to the loose enough hydrogel structure, which retains the stable, non-flowing gel structure for 6-24 months at the storage temperature of 4-25° C., but it is easy to inject through needles, like a 25G needle (inner diameter of needle 0.50 mm). 25G needle is minimally invasive in subcutaneous and intramuscular administrations that are the main administration routes for nucleotide or nucleoside analogue reverse transcriptase inhibitors, such as entecavir.

The combined composition of silica microparticles and silica sols that forms a stable and non-flowing hydrogel structure (that remains stable at rest, e.g., in a prefilled syringe) are shear-thinning and after shear (e.g., due to injection through a thin needle) and a short recovery time at 37° C., the combined compositions either turn again into a stable and non-flowing hydrogels or into a highly viscous, but slowly flowing dosage form. The preferable, stable and non-flowing hydrogel structure provides better possibilities to decrease the burst (initial fast release) due to a structure that keeps the silica microparticles tightly together in one three-dimensional entity within the hydrogel.

Foreign material such as microscopic particles is recognized and eliminated from the tissue by phagocytosing leukocytes. Typically, the recognition involves also an inflammatory reaction, which is not desirable for controlled drug release systems used e.g. for subcutaneous administration of drugs. Silica microparticles, which are embedded in the silica hydrogel, are more difficult to recognize by human leukocytes than silica microparticles alone, i.e., the silica hydrogel inhibits human leukocyte activation induced by the silica microparticles. Thereby, the combined hydrogel compositions prepared from silica microparticles and silica sol has a positive effect on tolerability and safety of silica depot formulations when injected locally in the tissue.

There is also another benefit in the silica-silica hydrogel composite of the present invention, which is based on the low solubility of silica. Amorphous silica, as the sol-gel derived silica microparticles and the silica hydrogel of the present inventions have a solubility of 130-150 ppm (mg/l) in neutral water (and only ca. 10-20% higher at e.g. pH 5) and thus also in simulated body fluids and in body fluids. This means that the silica microparticles dissolve only in a negligible amount in water phase of the hydrogel. It means that any water phase present in a system becomes quickly saturated with respect to silica and the dissolution of silica stops. As the encapsulation efficiency of the encapsulated active pharmaceutical ingredients (API), such as entecavir, is good in the silica microparticles of the present invention, i.e. the release of entecavir is mainly based on dissolution (degradation by dissolution in the water phase), it means that API is not released from the silica microparticles into the water phase of silica hydrogel, e.g. during the storage. The negligible release of API is further supported by the fact that the water is not present as a free phase, but a part of a dispersion structure (hydrogel) with restricted mobility of the liquid phase. This ensures that the silica microparticles control the release of API in tissue, where the body fluids flow and thus, the low solubility is no problem and the main task of the silica hydrogel is to ensure the long-term stability and easy-to-use and minimally invasive properties.

In the present invention, a continuous process bra flow process and continuous reactors (also called flow reactors), especially a continuous process in a tube reactor, is utilized before the form-giving, such as spray-drying, to better control the silica processing and encapsulation of the active pharmaceutical ingredients (API), such as nucleotide or nucleoside analogue reverse transcriptase inhibitor, into silica. In a typical case, silica sol and API (dissolved or dispersed in a liquid, typically in water with adjusted pH or in ethanol-water solutions) to be encapsulated are pumped as separate flows into a reactor where the 2 flows are combined. It is also possible that the precursor of silica, typically an alkoxysilane, such as tetraethoxysilane (also called tetraethyl orthosilicate, TEOS) or inorganic silicate solutions and API are pumped in one flow and water with adjusted pH in another flow. The compositions of the flows are adjusted depending on API properties to ensure the stability of API and good encapsulation. The continuous reactor can be a continuously-stirred tank reactor (CSTR), e.g., a beaker with a separate stirring or agitator system with constant inflows and outflows or corresponding or a tube reactor without mixing, i.e., a plug-flow reactor (PFR) with a laminar flow (a flow with no lateral mixing) or corresponding, or a tube reactor with mixing (the mixing may occur by a turbulent flow (a flow with cross-current currents perpendicular to the direction of flow) creating, e.g. swirls) or by separate mixing elements integrated in the tube reactor). The use of continuous reactors enables better adjustment of different reaction and aggregation rates of silica precursors and silica species than non-continuous reactors, e.g. a batch reactor (BR). In BR all reactions are let to occur, typically under stirring, but with no feed (inflows and outflows) before the desired reactions have occurred. In a typical case of the present invention, a continuous tube reactor is used to ensure that contact time between the silica sol and API is kept constant and short enough to ensure the solubility of API and/or desired degree of reactions and aggregation of silica species prior to form-giving. The form-giving process takes time, and if silica sol with one pH and API solution with another pH are mixed in a batch reactor and then pumped into the form-giving process, such as spray-drying, the contact time between the silica sol and API varies within the batch. If a spray-drying process takes 30 minutes, the first spray-dried microparticles are formed with 30 minutes shorter contact time between the silica sol and API than the last microparticles. The solubility of any substance is typically pH-dependent, but also the contact time affects the stability of the whole system, because the silica species in the silica sol react and aggregate with time. The optimal pH of the silica sol (e.g., with respect to the desired biodegradation rate of the silica dosage form after the form-giving) and API often differ from each other and the continuous reactors provide an option to better match these properties to result in good encapsulation and desired release profile for the encapsulated API.

The depot formulations according to the present invention are stored in syringes to keep the injectable hydrogel composites stable. Preferable syringes prevent a leakage of a vapour of the hydrogel composites (offer high moisture barrier), which ensures the stable injectability and release properties of the hydrogel composite during storage. The syringes according to the present invention may be made of a glass, plastic or composite, preferably glass.

Preferred Embodiments

In preferred depot formulations of the present invention the silica hydrogel composite is non-flowing and structurally stable hydrogel at 37° C. after the shear stress is applied by injection.

In preferred depot formulations of the present invention the silica sol has a solid content of ≤3 wt-%, preferably ≤2 wt-% and most preferably ≤1 wt-%.

In preferred depot formulations of the present invention the silica particles comprise from 0.1 to 70 wt-%, preferably from 0.3 to 50 wt-%, and most preferably from 1 to 15 wt-% of the incorporated nucleotide or nucleoside analogue reverse transcriptase inhibitor.

Typically the silica particles of the present invention are microparticles having a diameter between 0.5 µm and 300 µm, preferably 0.5 µm and 100 µm, more preferably 0.5 µm and 30 µm and most preferably 0.5 µm and 20 µm. The volume fraction of silica particles having a diameter <1 µm is typically <3%, preferably <2%, and most preferably <1 vol-%.

The hydrogel composite of depot formulation of the present invention typically comprises from up to 80 wt-r, preferably 10 to 80 wt-%, most preferably 20 to 60 wt-% of the silica particles.

The composite solid content of the depot formulation of the present invention is typically from 10 wt-% to 75 wt-%, preferably from 15 wt-% to 60 wt-% and most preferably from 25 wt-% to 55 wt-%.

The complex modulus of the depot formulation of the present invention measured under small angle oscillatory shear in the linear viscoelastic region is <2400 kPa, preferably <1200 kPa and most preferably <600 kPa.

The loss factor, i.e. viscous modulus/elastic modulus, of the depot formulation of the present invention typically is <1, preferably <0.8 and most preferably <0.6.

The measured viscosity of the depot formulation of the present invention is typically dependent on the shear rate employed. The viscosity typically is 10-50 Pas measured with a shear rate of 10-50 s$^{-1}$, 0.4-1.5 Pas measured with a shear rate of 200-210 s$^{-1}$, and 0.1-0.4 Pas measured with a shear rate of 600-610 s$^{-1}$.

The silica particles of the depot formulation can comprise more than one nucleotide or nucleoside analogue reverse transcriptase inhibitor.

The silica particles of the depot formulation of the present invention can be obtained with different processes. The process employed is typically selected from spray drying, single emulsion, double emulsion, polymerization, coacervation phase separation and solvent extraction methods, preferably spray drying, most preferably spray drying with continuous particle separation by a cyclone separator.

The silica particles of the depot formulation of the present invention can be selected from the group consisting of silica particles obtained by spray drying as such, silica fibre fragments and moulded or casted silica monoliths as such or as crushed.

The nucleotide or nucleoside analogue reverse transcriptase inhibitor, comprised in the silica particles of the depot formulation of the present invention is typically incorporated into the silica particles employing a continuous process within a tube reactor wherein said nucleotide or nucleoside analogue reverse transcriptase inhibitor and the silica sol are continuously fed as separate flows into and combined in said reactor, then continuously fed out of said tube reactor and into a continuous spray drying process with continuous particle separation by a cyclone separator.

The nucleoside analogue reverse transcriptase inhibitor, comprised in the silica particles of the depot formulation of the present invention is, in some embodiments of the present invention, selected from the group consisting of dideoxynucleosides.

The nucleotide or, nucleoside analogue reverse transcriptase inhibitor, comprised in the silica particles of the depot formulation of the present invention is, in some embodiments of the present invention, selected from the group consisting of zidovudine, didanosine, zalcitabine, stavudine, lamivudine abacavir, emtricitabine, entecavir, tenofovir, adefovir, apricitabine, elvucitabine, amdoxovir and racivir, preferably entecavir.

The nucleotide or nucleoside analogue reverse transcriptase inhibitor, comprised in the silica particles of the depot formulation of the present invention is, in some embodiments of the present invention, a deoxyguanosine analogue, preferably selected from the group consisting of hydroxymethyl(methylenecyclopentyl)purines and pyrimidines.

The depot formulation of the present invention is, typically selected from the group consisting of injectable formulations and implantable formulations, preferably injectable.

The depot formulation of the present invention is typically for administration selected from the group consisting of parenteral, preferably subcutaneous, intramuscular, peritoneal and ocular administration.

The depot formulation of the present invention is typically for administration from once a week to once a year, preferably once a month, to once every six months, and more preferably once every other month to once in three months, and most preferably once every three months.

The depot formulation of the present invention is typically for administration of a depot dose of the nucleotide or nucleoside analogue reverse transcriptase inhibitor being from 0.1 mg to 200 mg, preferably from 20 mg to 160 mg, more preferably from 30 mg to 120 mg and most preferably from 40 mg to 100 mg.

Use of the depot formulation of the present invention is typically for treatment of chronic viral infections and prevention of chronic viral reinfection. Preferably use of the depot formulation of the present invention is for viral infections selected from the group consisting of hepatitis B and HIV infections, and most preferably the group consisting of hepatitis B infections. Most preferably the depot formulation used for treatment of chronic viral infections and prevention of chronic viral reinfection comprises entecavir.

In preferred prefilled syringes of the present invention the weight loss of the syringe comprising the depot formulation after 2 weeks storage at 70° C. is less than 10 wt-%, preferably less than 5 wt-%, more preferably less than 3 wt-% of the original weight.

FIGURES

Figure 1:
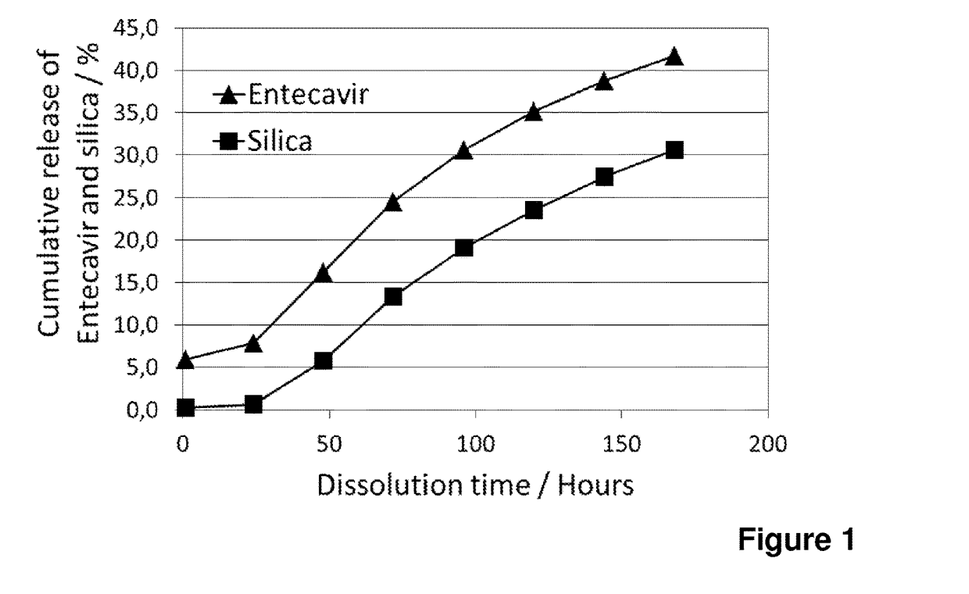
FIG. 1 illustrates cumulative release of entecavir and dissolution of silica from hydrogel composite after 3 months of storage in prefilled syringes in closed aluminum foil packages at 25° C. and relative humidity of 60%.

FIG. 2 illustrated average complex modulus (G*) for the hydrogel composites as a function of storage (25° C./60%) time.

FIG. 3 illustrates dynamic viscosity as a function of shear rates for the hydrogel composite formed from silica microparticles R10-120 MP (with 7% (w/w) loading of entecavir) and silica sol R400 (1 g of R10-120 MP in 1 ml of R400 sol) (A=fresh (=0 months), B=stored 3 months and C=stored 6 months in a syringe at 25° C. and 60% of relative humidity in a syringe closed in aluminium foil).

FIG. 4 illustrates loss factor (tan δ=G"/G') for the combined hydrogel compositions prepared from 0.5 g and 1.0 g silica microparticles in 1 ml of R400 silica sol simulating the structure in the syringe prior to the injection.

FIG. 5 illustrates loss factor (tan δ=G"/G') for the combined hydrogel compositions prepared from 0.5 g and 1.0 g silica microparticles in 1 ml of R400 silica sol after the stress (constant shear) simulating the structure, after the injection.

FIG. 6 illustrates individual plasma entecavir concentrations (ng/ml) by time (h) in 6 beagle male dogs administered with 36 mg of entecavir in the hydrogel composite of R15-126 microparticles and R400 silica sol.

FIG. 7 illustrates individual plasma entecavir concentrations (ng/ml) by time (h) in 6 beagle female dogs administered with 36 mg of entecavir in the hydrogel composite of R15-120 microparticles and R400 silica sol.

EXAMPLES

The following experimental section illustrates the invention by providing examples.

Example 1

Preparation of Injectable Hydrogel Composites with Encapsulated Entecavir from Silica Microparticles (MP) and Different Silica Sols (SS)

The sol-gel derived silica microparticles (MP) were prepared using TEOS (tetraethyl orthosilicate=tetraethoxysilane, Sigma-Aldrich) as a precursor for silica. The preparation of the silica microparticles with 7 wt-% of encapsulated entecavir started by preparation of an initial sol (molar ratio R=$H_2O$/TEOS=3, 10 or 15 at pH 2 (HCl was used to adjust the pH). The hydrolysis of TEOS was let to occur at room temperature (at 21-23° C.) for 25-30 min under continuous mixing. Next the silica sols were cooled down to 0° C. in order to avoid the gel formation. The silica sols and entecavir solutions (of which pH was adjusted to 9.7-10.1 using NaOH) were combined within 75-110 min after the hydrolysis by pumping the initial sol (R3, R10 or R15) and the entecavir solution into a separate vessel under mixing or into a cylindrical tube before the combined flow reached the nozzle of the spray dryer (Büchi, B-191 and GEA Mobile Minor). After the combination of the flows, the final molar ratio R=$H_2O$/TEOS was 120 and pH was 5.8-6.0 for all formulations (the molar ratio increased due to the water in the entecavir solution. Hence, the final formulations are expressed as R3-120, R10-120 and R15-120). The silica sol and the entecavir solution were in contact for about 4-6 minutes before reaching the nozzle (e.g., R3-120 with 7% (w/w) entecavir (4 min) or R3-120 with 7% (w/w) entecavir (6 min)). The combined flow was spray dried to silica microparticles with 7 wt-% of encapsulated entecavir (Spray dryer parameters; GEA Mobile Minor: Inlet temperature: 180-182° C.; Outlet temperature: 80-83° C.; Aspirator: 80 kg/h (Nitrogen); Atomization Pressure 1.5 Bar, Atomization flow 11.0 kg/h.

Co-current two-fluid nozzle: Nozzle 1.0 mm; Nozzle cap: 5.0 m and spacer: medium; Büchi B-191: Inlet temperature: 120° C.; Outlet temperature: 59-67° C.; Aspirator 32 $m^3$/h; Feed flow 3.4 ml/min; Atomization Flow: 700 l/h (Air)).

The silica sols (SS) to be mixed with the spray-dried silica microparticles were prepared using TEOS (tetraethyl orthosilicate=tetraethoxysilane, Sigma-Aldrich) as a precursor. A silica sol with R=$H_2O$/TEOS (molar ratio)=400, corresponding to about 0.9 wt-% of silica, was prepared and calculated, initial pH in every sample was pH 2 (HCl was used to adjust the pH). The hydrolysis was let to occur at room temperature (at 21-23° C.) for 25-65 min under continuous mixing prior to the cooling (to 0° C.) and pH adjustment of the sol. The pH was raised to 6.2 by adding 0.1 M NaOH with continuous stirring. After the pH adjustment the silica sols were mixed within 5-10 min with the spray-dried microparticles.

The silica microparticles and the silica sol were mixed under light stirring to avoid bubble formation. Concentration of the silica microparticles (MP) in the silica sols (SS) was 1.0 g/ml. The suspensions (the combined composition in the flowing form) formed from silica microparticles and silica sol were transferred into the plastic or glass syringes (BD Medical and Gerresheimer) by direct sucking of 1 or 10 ml of the combined composition into the syringe (without using a needle) or by using luer-lock adapters and the possible air bubbles were removed. The combined compositions turned into a hydrogel within minutes, in some cases within few hours after the filling. If the gel formation took several hours, the combined composition was kept stable by gentle mixing in a roller mixer.

Example 2

The In Vitro Release of Entecavir and Dissolution of Silica from Hydrogel Composites and Plain Silica Microparticles The release (in vitro) of entecavir and dissolution of silica from the hydrogel composite of R10-120 with 7% (w/w) of encapsulate entecavir and R400 silica sol was studied by immersing 20-30 mg of composite in 50 ml of 50 mM Tris buffer solution (pH7.4, 37° C.). The studies were conducted in sink conditions, i.e. at c(SiO$_2$)<30 ppm, i.e. at c(SiO$_2$) that is less than 20% of the solubility of the particular SiO$_2$ at the same. The cumulative release rates for the hydrogel composite stored in prefilled syringes (Glass syringes with leer-lock, 1 ml, Gerresheimer) in the closed aluminium foil packages after the storage of 3 months at 25° C. and 60% of relative humidity are illustrated in FIG. 1. The results show that the release rate of entecavir is about 0.25%/h indicating that the 100% is reached within about 17 days. This predicts the release rate of about 170 days, i.e. 5-6 months in vivo, as the common in vivo-in vitro correlation factor for the release from silica has been observed to be about 10 in subcutaneous, intramuscular and intraperitoneal administration. After the burst (initial fast release) release of entecavir, the release of entecavir and dissolution of silica proceed at about same rates, which indicates good encapsulation of entecavir in silica.

Example 3

Particle Size Distribution of the Spray Dried Silica Microparticles (R10-120 with 7% (w/w) of Entecavir)

The particle size distribution was determined using Sympatec (HELOS H2296) with the wet cell cuvette (lens R3 (0.5-175 um); dispersant ethanol; sonication time 30 s (100% power); optical density 15-20%; measurement time 20 s; stirrer rate at maximum (1000)) or using Sympatec HELOS H2370 equipped with a CUVETTE disperser and the R3 lens ranging from 0.5/0.9 to 175 μm. The Particles in Liquid (PIL) method was employed using ethanol as solvent. A few milligrams of the sample is taken from the sample vials and dispersed to a concentrated stock suspension of about 10-20 ml of ethanol. The CUVETTE disperser chamber was filled with ethanol and a magnetic stirrer (1000 rpm) was placed on the bottom of the cuvette. A reference baseline measurement was made with ethanol only. In a measurement a suitable sample is taken with a volumetric pipette from the stock suspension and pipetted to the CUVETTE disperser to obtain an optical concentration between 15-25%. When a measurement is started the sample is sonicated automatically for 30 s and paused when the measurement starts. A measurement last for 20 s and a particle size distribution is generated. Three parallel samples are taken from the stock solution and analysed in the above-described manner. The results are summarised in Table 1.

TABLE 1

Particle size of silica microsphere formulations with encapsulated entecavir.

| Microsphere formulation | Average D10 (μm) | Average D50 (μm) | Average D90 (μm) |
|---|---|---|---|
| R10-120 with 7% (w/w) of entecavir | 1.90 | 3.99 | 11.59 |
| R15-120 with 7% (w/w) entecavir | 2.10 | 4.65 | 11.58 |
| R3-120 with 7% (w/w) entecavir (4 min) | 1.75 | 3.57 | 7.15 |
| R3-120 with 7% (w/w) entecavir (6 min) | 1.83 | 3.77 | 7.88 |

Example 4

Rheological Measurements Tests and Injectability Tests for Injectable Hydrogel Composites of Silica Microparticle with Encapsulated Entecavir and Silica Sols Showing Both Stable Hydrogel Structure in the Syringe and Shear-Thinning Behaviour Under Shear Rheological measurements were conducted with a single rotational rheometer (ThermoHaake RS 300) equipped with a parallel-plate with a HPP20 TC measuring geometry (D=20 mm). This system was used to measure all materials. A CS/CR rotatory ramp-program with a gap of 0.3 mm and shear rate ranging from 0.1000 1/s to 1000 1/s at 25° C. was used to measure dynamic viscosity. Oscillatory testing (for loss factor and elastic and viscous moduli) was conducted with a frequency sweep with frequency range of 0.01-10 Hz at 25° C. with a 0.4 mm gap. Furthermore the testing was conducted under controlled deformation where the deformation was set to 0.002 which was previously determined with an amplitude sweep program.

Figure 2:
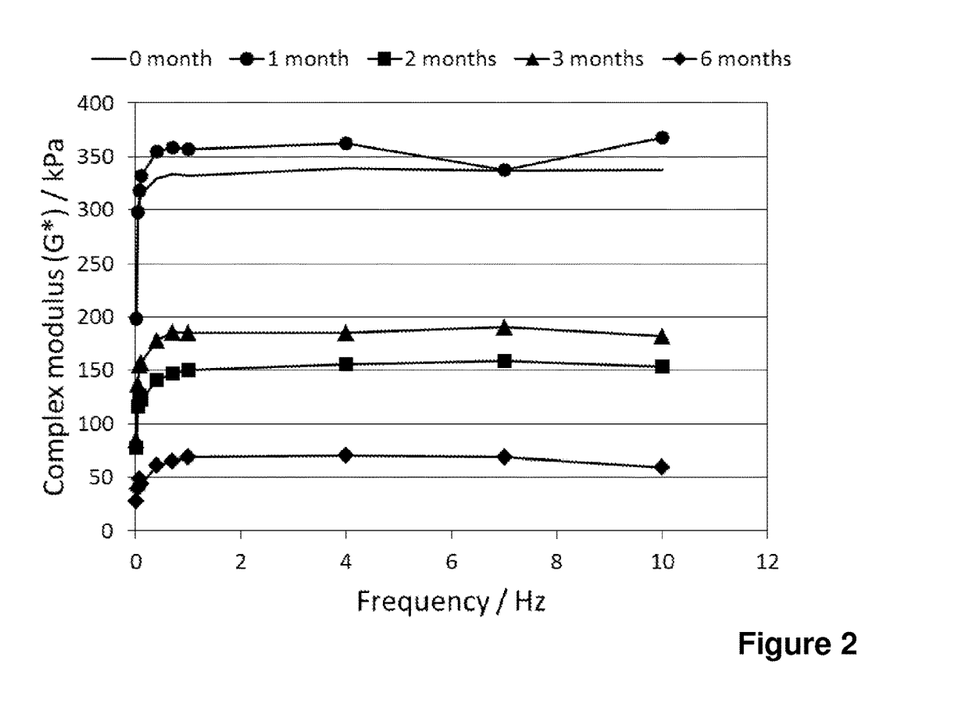

The oscillatory measurements were conducted to, show the stability of the hydrogel composite (of R10-120 silica microspheres with 7 wt-% of encapsulated entecavir and R400 silica sol, 1 g microspheres in 1 ml of silica sol) in a prefilled syringe as a function of storage time (0-6 months), which shows the ready-to-use nature of the product. The samples for the rheological measurements were taken from 3 different locations in the syringe. Due to minimal stress and shear in the oscillatory measurements, the dynamic viscosity measurements were conducted for the same samples that were used in the oscillatory measurements by continuing with the rotational shear for dynamic viscosity right after the oscillatory measurements. All measurements were conducted at 25° C. The rheological measurements were conducted for the fresh hydrogel composite (0 months) and for the hydrogel composite stored in prefilled syringes (Glass syringe, 1 ml, Gerresheimer) in the closed aluminium foil packages after the storage of 1, 2, 3, and 6 months at 25° C. and 60% of relative humidity. The ratio of viscous (G″) and elastic (G′) moduli, loss factor (loss tangent, tan δ=G″/G′) and complex moduli G* are shown in Table 2 and FIG. 2, show the gel-like structure of the composite (elastic modulus is larger than viscous modulus and loss factor is less than 1. For viscoelastic materials loss factor greater than 1 indicates that a material behaves more like a liquid and loss factor less than 1 means that a material behaves more like a solid, e.g., like a gel. For the hydrogel composites all loss factors are clearly less than 1. The gel-like structure ensures that the microparticles do no sediment in the syringe and the composite remains stable.

TABLE 2

Average loss factors (tan δ = G″/G′) and injection tests for the hydrogel composites as a function of storage (25° C./60%) time

| Frequency in Hz | 0 month | 1 month | 2 months | 3 months | 6 months |
|---|---|---|---|---|---|
| 0.01 | 0.44 | 0.45 | 0.51 | 0.55 | 0.67 |
| 0.04 | 0.25 | 0.22 | 0.18 | 0.19 | 0.47 |
| 0.07 | 0.17 | 0.25 | 0.20 | 0.22 | 0.24 |
| 0.1 | 0.13 | 0.16 | 0.19 | 0.20 | 0.33 |
| 0.4 | 0.06 | 0.08 | 0.16 | 0.14 | 0.20 |
| 0.7 | 0.04 | 0.05 | 0.11 | 0.09 | 0.16 |
| 1 | 0.03 | 0.04 | 0.08 | 0.06 | 0.18 |
| 4 | 0.05 | 0.07 | 0.09 | 0.08 | 0.16 |
| 7 | 0.04 | 0.11 | 0.07 | 0.05 | 0.12 |
| 10 | 0.04 | 0.05 | 0.08 | 0.10 | 0.17 |
| Injection, needle | 24G | 25G | 25G | 25G | 25G |

Figure 3:
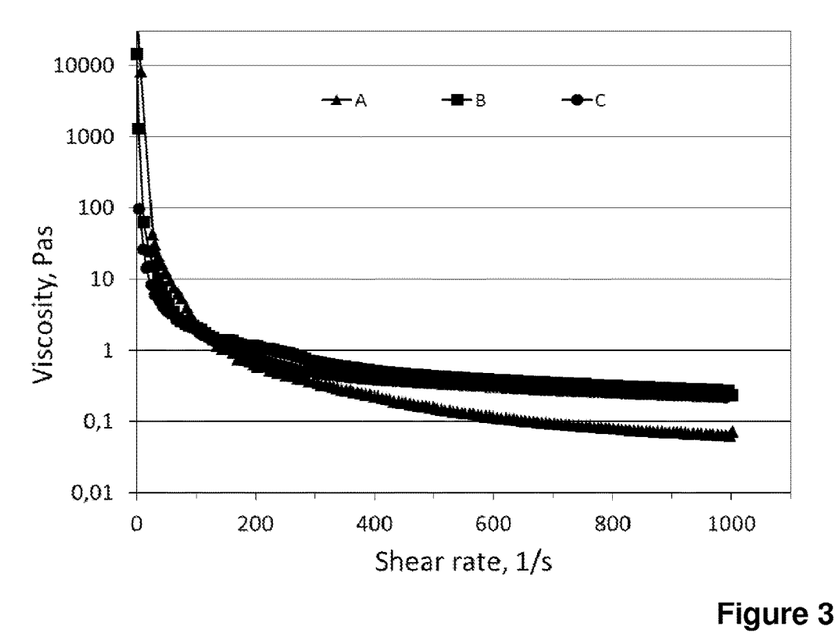

Although the hydrogel composite structure is a gel-like structure and remains stable as stored, the gel structure is so loose that it can injected through thin needles with inner diameters of 0.50 and 0.55 mm (24G: 0.55 mm×25 mm, 25G: 0.50 mm×25 mm, Terumo) as shown in Table 2. This is also supported by the clear shear thinning behaviour, which is observed in the dynamic viscosity measurements at different shear rates (Table 3 and FIG. 3). The shear thinning behaviour was clear for the fresh samples (0 months) as well as for samples stored in prefilled syringes in the closed aluminium foil packages after the storage of 3 and 6 months at 25° C. and 60% of relative humidity

TABLE 3

Dynamic viscosity at different shear rates after 0-6 months of storage

| Shear rate, 1/s | Dynamic viscosity, Pas |
|---|---|
| 42-49 | 13-46 |
| 200-210 | 0.4-1.5 |
| 600-605 | 0.1-0.4 |

Example 5

Preparation of Injectable Hydrogel Composites Prepared from Silica Microparticles (MP) and Different Silica Sols (SS) for Thin Needle Injections The placebo compositions (hydrogel composites) were made in a corresponding manner as described in Example 1. The preparation of the placebo silica microparticles started by preparation of an initial sol (molar ratio $R=H_2O/TEOS=10$ at pH 2, HCl was used to adjust the pH). After the hydrolysis the initial silica sol (R10) and ethanol (99%) were pumped into a cylindrical tube before the combined flow reached the nozzle of the spray dryer (GEA Mobile Minor). The silica sol and ethanol were in contact for 4 minutes before reaching the nozzle. After the combination of the flows, the final molar ratio corresponded to $R=H_2O/TEOS=50$ (i.e. the final formulation was R10-50; same volume of ethanol was used as water is needed to obtain R50 from the initial R10). The placebo formulation was designed to be a reference material for the silica microparticle formulation R10-120 with 7 wt-% of encapsulated entecavir, i.e. to obtain the same dissolution (biodegradation) rate of silica as for R10-120 with 7 wt-% of encapsulated entecavir.

The silica sols (SS) to be mixed with the spray-dried silica microparticles were prepared in a corresponding manner as in Example 1. $R=H_2O/TEOS$ (molar ratio) of the silica sols varied between R300-400 (R300, R350, R400), and the initial pH in every sample was pH 2 (HCl was used to adjust the pH). The hydrolysis was let to occur at room temperature (at 21-23° C.) for 25 min under continuous mixing. The pH was raised to 6.2 by adding 0.1 M NaOH with continuous stirring. After the pH adjustment the silica sols were mixed within 5-15 min with the spray-dried microparticles or they were aged for 3 hours at 40° C. prior to mixing.

The silica microparticles and the silica sol were mixed under light stirring to avoid bubble formation. Concentration of the silica microparticles (MP) in the silica sols (SS) varied between 0.15-1.0 g/ml. The suspensions (the combined composition in the flowing form) formed from silica microparticles and silica sol were transferred into the glass syringe (without using a needle) by direct sucking of the combined composition and the possible air bubbles were removed. The combined compositions turned into a hydrogel within few hours after the filling. Before the hydrogel formation, the combined composition was kept stable by gentle mixing in a roller mixer.

Only concentrations of the silica microparticles (MP) in the silica sols (SS) that varied between 0.5-1.0 g/ml formed hydrogels. With the concentrations of 0.5 g/ml it was possible to inject the combined composition through a 27G needle (0.4×20 mm), but the structure of the hydrogel composite was partly disintegrated. The best result, injection through a 30G needle (0.3×13 mm) was obtained with 0.75 g/ml of the silica microparticles (MP) in R400 silica sols (SS).

Example 6

Rheological Measurements for Injectable Hydrogel Composites Prepared from Silica Microparticles with Encapsulated Entecavir and Silica Sol Showing Both Stable Hydrogel Structure in the Syringe, Shear-Thinning Behaviour Under Shear and Stable Hydrogel or Flowing Structure after the Shear and Recovery.

The R3-120 silica microparticles with 7 wt-% of encapsulated entecavir and silica sol to be mixed with the silica microparticles were prepared as described in Example 1. A fresh (not aged) silica sol with $R=H_2O/TEOS$ (molar ratio)=400 was used and the concentrations of the said silica microparticles were 0.5 g and 1.0 g in 1 ml of R400 silica sol. As the combined compositions of silica microparticles in the R400 silica sol were still flowing, they were transferred into Gerresheimer 1 ml Luer-Lock glass syringes. The combined compositions were kept under gentle mixing in a roller mixer for 24 hours to avoid sedimentation of the microparticles. The combined compositions turned into hydrogels during the 24 hours in a roller mixer.

Figure 4:
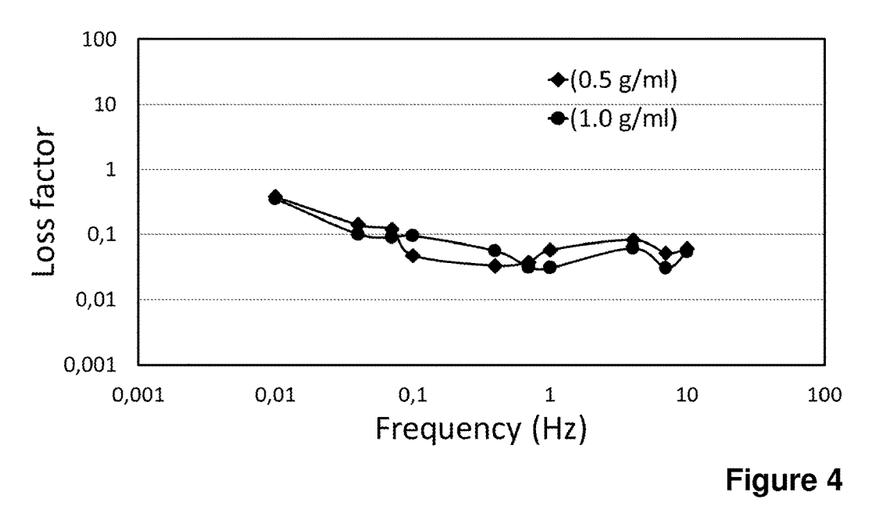

Rheological measurements were conducted with a single rotational rheometer (ThermoHaake RS 300) equipped with a parallel-plate measuring geometry (D=20 mm) and with a gap of 0.3 mm. The rheological measurements for the unstressed materials (combined compositions in the syringes) were conducted at 25° C. and for the stressed (constant shear rate simulating the injection through a thin needle) materials at 37° C. To show the stable hydrogel structure in the syringe, oscillatory testing (for loss factor and elastic and viscous moduli) within the linear viscoelastic region (strain 0.002) was conducted with a frequency sweep with the frequency range of 0.01-10 Hz at 25° C. The ratio of viscous (G″) and elastic (G′) moduli, loss factor (loss tangent, tan δ=G″/G′) for both of the combined compositions of 0.5 g and 1.0 g silica microparticles in 1 ml of R400 silica sol is clearly lower than 1 (average of 3 parallel measurements indicated in FIG. 4) showing a stable, non-flowing hydrogel structure.

Figure 5:
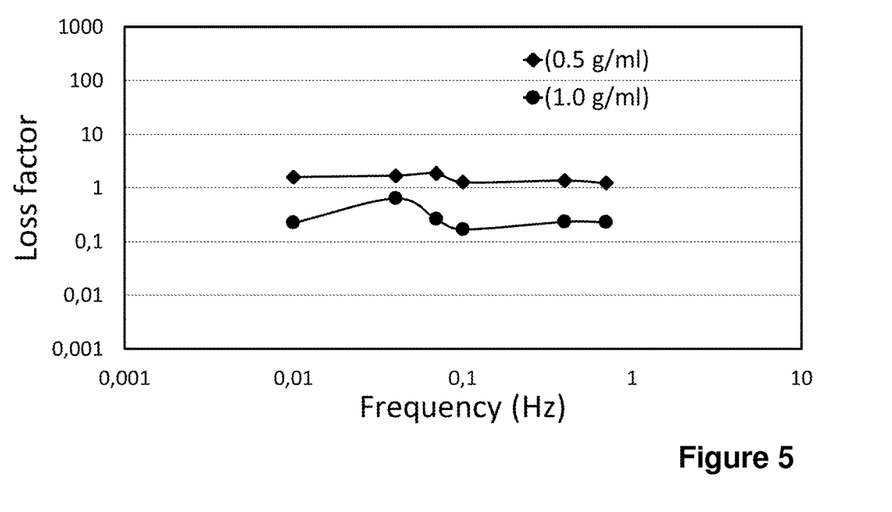

The combined compositions were then stressed under the controlled shear rate program (50 1/s for 10 s for homogenization followed by 5000 1/s for 30 s to simulate the injection followed by 1.0 1/s for 10 s for recovery). Right after the recovery another oscillatory testing (for loss factor and elastic and viscous moduli) within the linear viscoelastic region (strain 0.002) was conducted with a frequency sweep with the frequency range of 0.01-1.0 Hz at 37° C. The loss factor is clearly lower than 1 for the combined composition of 1.0 g of silica microparticles in 1 ml of R400 silica sol, but not for the combined composition of 0.5 g of silica microparticles in 1 ml of R400 silica sol having loss factor greater than 1 (average of 3 parallel measurements indicated in FIG. 5). The combined composition of 1.0 g of silica microparticles in 1 ml of R400 silica sol is a stable hydrogel structure also after the stress (constant shear) that simulates the injection, but the combined composition of 0.5 g of silica microparticles in 1 ml of R400 silica sol has turned into a highly viscous, flowing composition.

Example 7

Release of Entecavir from the Combined Composition Hydrogel Composite) of the Silica Microspheres and Silica Sol In Vivo The combined composition (hydrogel composite) of R15-120 microspheres with 7% (w/w) of entecavir and R400 silica sol (36 mg/ml of entecavir in the final hydrogel composite) in prefilled syringes was administered subcutaneously in 12 (6 male and 6 female) beagle dogs. The ready-to-use syringes with fill volume of 1 ml were used to study the pharmacokinetics of 36 mg entecavir in a single dose. After the administration, the animals were followed for 91 days. Blood samples from a jugular vein were collected from the animals to determine the plasma levels of entecavir before administration and at 30 min, 1 h, 2 h, 4 h, 8 h and 24 h on day 1 and once on days 3, 5, 7, 11, 15, 29, 43, 57, 71, 85, and 91. Canine K2-EDTA plasma samples were prepared for analysis by performing protein precipitation and phospholipid removal. The frozen plasma samples were thawed and tempered at room temperature. Phenomenex Phospholipids Removal Plates were used for sample extraction. Before pipetting the plasma samples, each well was activated with 1 ml of acetonitrile. Acetonitrile was eluted using vacuum. Then 200 µl of the plasma samples were transferred into the wells. 40 µl of the internal standard solution (lamivudine, 100 ng/ml) was added. Next, 760 µl of acetonitrile was added and the plate was covered with parafilm. The plate was shaken in the horizontal plane for 2 min. The samples were eluted using vacuum, and the extracts were evaporated to dryness in a sample collection well plate at +50° C. under a gentle stream of nitrogen. The residue was dissolved in 200 µl of a mixture of DMSO and water (10:90, v/v) containing 0.1% formic acid. The plate was shaken horizontally for 10 min. After transfer into inserts of autosampler vials, the samples were centrifuged for 2 min at 2000 rpm in a microcentrifuge. Finally, the samples were injected (10 µl) into the HPLC-MS/MS system.

Separations were performed with a Waters XSelect® HSS T3 2.1×150 mm (3.5 µm) column coupled with an integrated Waters XSelect® HSS T3 2.1×10 mm guard cartridge. The mobile phase consisted of two eluents: A was 0.1% formic acid in water and B was 0.1% formic acid in methanol. A chromatographic run with a gradient was used: 0 min→1 min A was 92.5% (isocratic); from 1 min to 2 min A was decreased from 92.5% to 5%, from 2 min to 3 min A was 5% (isocratic), from 3 min to 4 min A was increased from 5 to 92.5% and lastly A was held constant at 92.5% from 4 min to 7 min. The column oven was set to +25° C. Mass spectrometric detection was carried out using an API Sciex 4000 QTrap mass spectrometer with positive Turbo Ion Spray (TIS) ionisation and multiple reaction monitoring (MRM) mode. TIS temperature was +505° C. The nebulizer gas (Gas 1) setting was 50 and the turbo gas (Gas 2) setting was 50. The TIS voltage setting was 4900 V. The declustering potentials were 60 V for entecavir and 59 V for the internal standard. Entrance potential was set to 10 V for both molecules. Collision energy was 25 V for entecavir and 24 V for the internal standard. Curtain gas (nitrogen) was set to value 10 and collision gas (nitrogen) was set to value 5.0. The precursor ion-fragment ion pairs detected were m/z 278.1-152.0 for entecavir and m/z 230.0-111.9 for the internal standard. The dwell time for both molecules was 250 msec. The data from the HPLC-MS/MS analyses were collected using Applied Biosystems Analyst 1.6.1 software. The peak integrations, calibration curves and quantitations were generated with the same software. The statistics were calculated with Microsoft Excel 2010 software. The standard curves were generated using weighted $(1/x^2)$ linear regression. The plasma concentration data were modelled with Phoenix WinNonlin 6.4 software (Certara Pharsight) using non-compartmental analysis.

Figure 6:
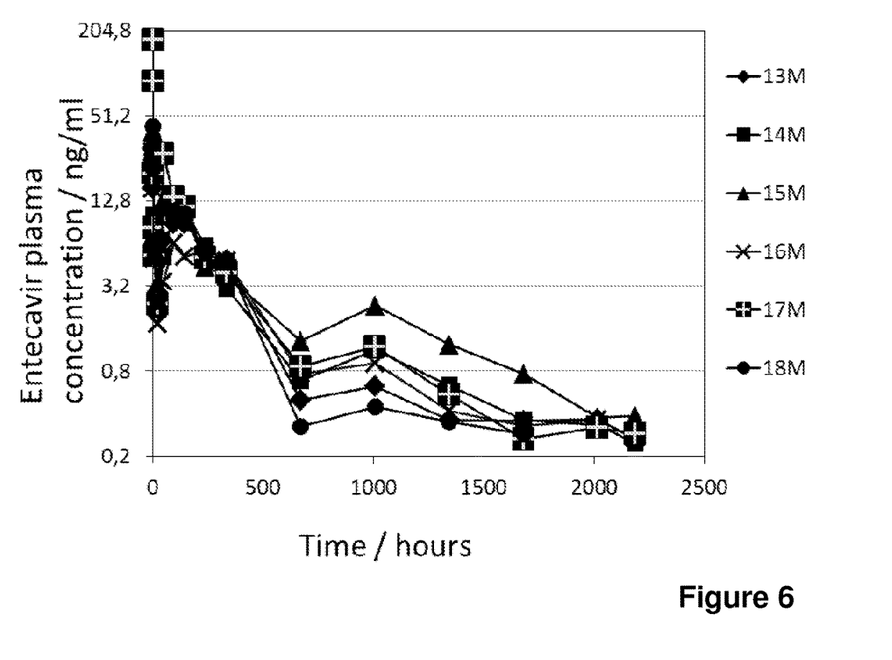
Figure 7:
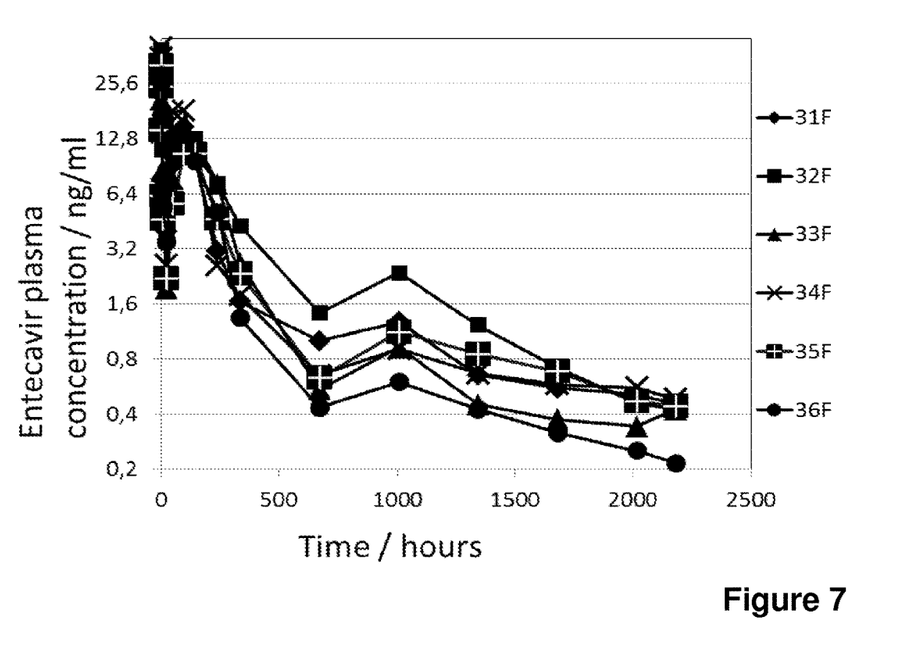

The individual concentrations by time curves are depicted in FIGS. 6 and 7. The initial absorption of entecavir from the site of injection was rapid when dosed as silica depot formulation, and $C_{max}$ was observed at 30 to 60 min post injection. Thereafter the plasma entecavir concentration decreased close to 1 ng/ml level, on average, by day 29. After this time point a clear sustained release phase was observed for the next two months (up to day 91) with gradually decreasing plasma entecavir concentration.

Example 8

Prefilled Syringes Keeping the Injectable Hydrogel Composites Prepared from Silica Microparticles with Encapsulated Entecavir and Silica Sol Stable.

The stability of the combined compositions of 1.0 g of silica microparticles (R3-100) with 7 wt-% of encapsulated entecavir in 1 ml of R400 silica sol and R400 silica sol as such were studied in two different types of syringe systems. The formed injectable hydrogels composites were stored in prefilled syringes (Glass syringes with a luer lock and a separate plunger stopper of rubber, 1 ml, ClearJect syringe, Gerresheimer Bünde GmbH) in the closed aluminium foil packages at (4° C., 25° C./60% and at 40° C./65%) for 6 months with minor changes in the general structure (visual observation), injection and entecavir release properties. When the same hydrogel composite was stored in prefilled plastic syringes (BD 1 ml Syringe Luer-LoK™ Tip sealed with plastics Monoject™ Syringe Tip Caps, Coviden IIc) in the closed aluminium foil packages (at 40° C./65%) for 2 months, the hydrogel composite was dried in the syringe and it was not possible to inject the material through a thin needle.

In another test series 500 microliters of R400 silica sol was injected into 3 different types of syringe systems (5 parallel samples for each syringe systems):

Glass syringe: ClearJect 1 ml syringe, Gerresheimer Bünde GmbH

Plastic syringe: Plajex™ 1 ml syringe, Terumo

Plastics syringe: BD 1 ml Syringe Luer-Lok™ Tip with Monoject™ Syringe Tip Caps, Coviden IIc The syringes were kept at enhanced conditions at 70° C. for two weeks and the weight of the syringes was monitored as a function of time to find out whether vapour is leaking out from the syringe. After two weeks the Gerresheimer glass syringe has retained 98% of the original weight, the plastic syringe of Terumo 96.8% and the plastic syringe of BD 83.5%. The results indicate that a syringe with a minor vapour leakage (high moisture barrier), such as the glass syringe of Gerresheimer is of importance to ensure the stability of the injectable hydrogel composite comprising silica microparticles and silica sot.

Example 9

Silica Hydrogel Inhibits Human Leukocyte Activation by Silica Microparticles

The interaction between human peripheral blood leukocytes and silica microparticles was studied. Silica placebo microparticles were produced as described in Examples 1 and 5. Peripheral blood was obtained by venipuncture using EDTA as anticoagulant from healthy adult donors. The leukocyte fraction was separated using dextran sedimentation (1 ml 6% Dextran in 9 ml blood) at room temperature. The leukocyte rich plasma layer was washed twice with $Ca^{2+}$ and $Mg^{2+}$ free HBSS-buffer supplemented with 0.1% gelatin (CMF-HBSS) and finally resuspended in ca. 1 ml of CMF-HBSS. The leukocyte concentration was determined by using a Bürker chamber and microscope. A luminol enhanced chemiluminescence (CL) method was used to investigate the reaction between leukocytes and silica microparticles. The CL response was measured using Victor$^2$ multilabel counter at 425 nm in 96 well black plastic plates at 37° C. for 60 min. Typically, the reaction mixture contained 300 000 leukocytes and 0.5 mM luminol in 0.2 ml gel-HBSS buffer either with or without silica microparticles. Silica microparticles induced a clear dose dependent CL response in leukocytes. The highest activation was seen at silica microparticle concentration range 1-10 mg/ml, which was typically 100-1000 fold higher than the CL response of the same cells without any activation stimulus.

To test the effect of silica hydrogel on silica microparticles induced leukocyte CL, R400 silica hydrogel was prepared as described in Example 1, and it was allowed to age for 7 days and then redispersed and mixed with the silica microparticles. It was found that R400 hydrogel at 25% concentration in the CL reaction mixture inhibited the leukocyte CL response triggered by 1.25 and 6.25 mg/ml silica microparticles by 30-40%, on average.

Example 10

Silica Hydrogel Inhibits Microparticle Uptake by Human Leukocytes

To investigate the phagocytosis of silica microparticles by human leukocytes, peripheral blood was collected from healthy adult volunteers and leukocytes were isolated as described in Example 9. To measure phagocytosis of silica microparticles, the microparticles, prepared as described in Example 9, were loaded with fluorescein, which emits fluorescent light at 530 nm when triggered with laser light at 488 nm. Leukocytes (300 000 cells) were incubated with 1.25 mg/ml fluorescein loaded silica microparticles in 0.5 ml gel-HBSS buffer at 37° C. up to 60 min and the phagocytosis reaction was stopped by cooling the samples quickly in an ice bath at various time points. The samples were analysed using FACSCalibur flow cytometer. The polymorphonuclear leukocyte fraction was gated with the help of phycoerythrin labeled anti-CD16 monoclonal antibody that recognizes phagocytic leukocytes expressing Fc gamma receptor type 3. Only the CD16 positive cells were analysed for phagocytosis. For each sample, 10 000 cells were collected and analysed for fluorescence signal originating from fluorescein in silica microparticles. Typically, after 60 min incubation with fluorescein silica microparticles, more than 40% of the cells analysed were binding microparticles.

When R400 silica hydrogel, prepared as described in Example 9, was added in the phagocytosis reaction mixture (at 1.56% concentration), the percentage of microparticle binding cells was decreased to ca. 20%, indicating about 50% reduction in cells recognizing silica microparticles. This shows that R400 silica hydrogel is able to prevent the recognition of silica microparticles by human leukocytes and thereby has a positive effect on tolerability and safety of silica depot formulations when injected locally in the tissue.

Other Preferred Embodiments

It will be appreciated that the composites and methods of the present invention can be incorporated in the form of a variety of embodiments, only a few of which are disclosed herein. It is e.g. apparent for the expert skilled that embodiments of the composites and methods have corresponding method and composite, respectively, embodiments. It will be apparent for the expert skilled in the field that other embodiments exist and do not depart from the spirit of the invention. Thus, the described embodiments are illustrative and should not be construed as restrictive.

The invention claimed is:

1. A depot formulation comprising a biodegradable silica hydrogel composite incorporating a nucleotide or nucleoside analogue reverse transcriptase inhibitor, wherein the silica hydrogel composite is obtainable by mixing
   a) silica particles comprising said nucleotide or nucleoside analogue reverse transcriptase inhibitor and having a maximum diameter of ≤1,000 µm, as such or as a suspension, with
   b) a silica sol wherein
   i) said silica sol has a solid content of ≤5 wt-%,
   ii) said silica hydrogel composite comprises up to 85 wt-% of said silica particles, and
   iii) said hydrogel composite is non-flowing and structurally stable when stored at rest and shear-thinning when shear stress is applied by injection.

2. The depot formulation of claim 1, wherein the silica hydrogel composite is non-flowing and structurally stable hydrogel at 37° C. after the shear stress is applied by injection.

3. The depot formulation of claim 1, wherein the silica sol has a solid content of ≤3 wt %.

4. The depot formulation of claim 1, wherein the silica particles comprise from 0.1 to 70 wt % of the incorporated nucleotide or nucleoside analogue reverse transcriptase inhibitor.

5. The depot formulation of claim 1, wherein the silica particles are microparticles having a diameter between 0.5 µm and 300 µm.

6. The depot formulation of claim 5, wherein the volume fraction of silica particles having a diameter <1 µm is <3% vol-%.

7. The depot formulation of claim 1, wherein the hydrogel composite comprises from up to 80 wt % of the silica particles.

8. The depot formulation of claim 1, wherein the composite solid content is from 10 wt-% to 75 wt %.

9. The depot formulation of claim 1, wherein the complex modulus measured under small angle oscillatory shear in the linear viscoelastic region is <2400 kPa.

10. The depot formulation of claim 1, wherein the loss factor is <1.

11. The depot formulation of claim 1, wherein the viscosity is 10-50 Pas measured with a shear rate of 10-50 $s^{-1}$, the viscosity is 0.4-1.5 Pas measured with a shear rate of 200-210 $s^{-1}$, and 0.1-0.4 Pas measured with a shear rate of 600-610 $s^{-1}$.

12. The depot formulation of claim 1, wherein the silica particles of the depot formulation comprise more than one nucleotide or nucleoside analogue reverse transcriptase inhibitor.

13. The depot formulation of claim 1, wherein the silica particles are obtained with a process selected from spray drying, single emulsion, double emulsion, polymerization, coacervation phase separation and solvent extraction methods.

14. The depot formulation of claim 1, wherein the silica particles are selected from the group consisting of silica particles obtained by spray drying as such, silica fibre fragments and moulded or casted silica monoliths as such or as crushed.

15. The deport formulation according to claim 13, wherein the nucleotide or nucleoside analogue reverse transcriptase inhibitor, comprised in the silica particles, is incorporated into the silica particles employing a continuous process within a tube reactor wherein said nucleotide or nucleoside analogue reverse transcriptase inhibitor and the silica sol are continuously fed as separate flows into and combined in said reactor, then continuously fed out of said tube reactor and into a continuous spray drying process with continuous particle separation by a cyclone separator.

16. The depot formulation according to claim 1, wherein the nucleoside analogue reverse transcriptase inhibitor is selected from the group consisting of dideoxynucleosides.

17. The depot formulation according to claim 1, wherein the nucleotide or nucleoside analogue reverse transcriptase inhibitor is selected from the group consisting of zidovudine, didanosine, zalcitabine, stavudine, lamivudine abacavir, emtricitabine, entecavir, tenofovir, adefovir, apricitabine, elvucitabine, amdoxovir and racivir.

18. The depot formulation according to claim 1, wherein the nucleotide or nucleoside analogue reverse transcriptase inhibitor is a deoxyguanosine analogue.

19. The depot formulation according to claim 1, wherein said depot formulation is selected from the group consisting of injectable formulations and implantable formulations.

20. The depot formulation according to claim 1, wherein the formulation is for parenteral administration.

21. The depot formulation according to claim 1, wherein the formulation is for administration from once a week to once a year.

22. The depot formulation according to claim 1, wherein the formulation is for administration of a depot dose of the nucleotide or nucleoside analogue reverse transcriptase inhibitor being from 0.1 mg to 200 mg.

23. A prefilled syringe, wherein said prefilled syringe comprises the depot formulation according to claim 1.

24. The prefilled syringe according to claim 23, wherein the weight loss of the syringe after 2 weeks storage at C is less than 10 wt % of the original weight.

* * * * *